United States Patent [19]

Furlenmeier et al.

[11] Patent Number: 5,359,057
[45] Date of Patent: Oct. 25, 1994

[54] ACYLATION OF AMINES

[75] Inventors: André Furlenmeier, Basel; Urs Weiss, Pratteln, both of Switzerland

[73] Assignee: Hoffmann-La Roche Inc., Nutley, N.J.

[21] Appl. No.: 822,173

[22] Filed: Jan. 16, 1992

Related U.S. Application Data

[63] Continuation of Ser. No. 499,839, Mar. 27, 1990, abandoned, which is a continuation of Ser. No. 11,795, Feb. 6, 1987, abandoned.

[30] Foreign Application Priority Data

Feb. 7, 1986 [CH] Switzerland ................ 487/86

[51] Int. Cl.$^5$ ................ C07D 501/06; C07D 499/12
[52] U.S. Cl. ................ 540/222; 540/221; 540/225; 540/227; 540/314
[58] Field of Search ............ 540/222, 225, 227, 221, 540/314

[56] References Cited

U.S. PATENT DOCUMENTS

| 4,258,041 | 3/1981 | O'Callaghan et al. | 424/246 |
|---|---|---|---|
| 4,593,022 | 6/1986 | Labeeuw et al. | 514/206 |
| 4,641,819 | 9/1986 | Nagai et al. | 540/222 |
| 4,716,227 | 12/1987 | Furlenmeier | 540/230 |
| 4,767,852 | 8/1988 | Ascher | 540/222 |
| 4,826,972 | 5/1989 | Prager | 540/225 |
| 4,868,294 | 9/1989 | Brundidge et al. | 540/225 |

FOREIGN PATENT DOCUMENTS

| 20048915 | 4/1982 | European Pat. Off. . |
|---|---|---|
| 20057422 | 8/1982 | European Pat. Off. . |
| 20060745 | 9/1982 | European Pat. Off. . |
| 0088853 | 11/1982 | European Pat. Off. . |
| 115770 | 1/1984 | European Pat. Off. . |
| 187209 | 10/1985 | European Pat. Off. . |
| 3433147 | 3/1985 | Fed. Rep. of Germany . |
| 2027691 | 5/1979 | United Kingdom . |

Primary Examiner—Nicholas S. Rizzo
Attorney, Agent, or Firm—George M. Gould; George W. Johnston; Ellen Ciambrone Coletti

[57] ABSTRACT

There is described a process for the manufacture of carboxylic acid amides by acylating amines with 2-benzothiazolyl thioesters of carboxylic acids, which process comprises reacting the amine in the form of an acid addition salt. This process is especially of great advantage when the amine is not particularly stable in the form of the free base, which is frequently the case especially with 7-aminocephalosporin derivatives. 7-Acylamino-cephalosporin derivatives can be manufactured in good yield and in high purity with the novel process.

11 Claims, No Drawings

ACYLATION OF AMINES

This is a continuation, of application Ser. No. 07/499,839 filed Mar. 27, 1990 now abandoned, which is a continuation of Ser. No. 07/011,795, filed Feb. 6, 1987, now abandoned.

BRIEF SUMMARY OF THE INVENTION

This invention relates to a process for making carboxylic acid amides by acylating amines with 2-benzothiazoyl thioesters of carboxylic acids, wherein the amine reacted is in the form of an acid addition salt.

In a preferred process embodiment, the amine employed is not stable as a free base. For example, 7-amino-cephalosporin derivatives, which are frequently not stable in the free base form, can be employed in the process of the invention to obtain 7-acylamino-cephalosporin derivatives in good yield and with high purity.

DETAILED DESCRIPTION OF THE INVENTION

The invention is Concerned with a process for the manufacture of carboxylic acid amides by acylating amines with 2-benzothiazolyl thioesters of carboxylic acids, which process comprises reacting the amine in the form of an acid addition salt.

The acylation of amines with 2-benzothiazolyl thioesters is a method for the manufacture of carboxylic acid amides which is known per se. In this method the amine is used in the form of the free base, whereby an additional organic base, usually a tertiary amine, is frequently added to the reaction mixture in order to accelerate the course of the reaction. In cases in which an acid addition salt of an amine has been used as the starting material, it has hitherto been the belief that at least one equivalent of an organic base, usually a tertiary amine, must be added to the reaction mixture in order to convert the acid addition salt into the reactive form, i.e. into the free base.

It has now surprisingly been found that acid addition salts of amines can be reacted directly with 2-benzothiazolyl thioesters of carboxylic acids, i.e. that it is not necessary previously to neutralize the acid addition salt of the amine with an organic base in order to liberate the reactive form, namely the free amine. As the Examples hereinafter demonstrate, the process in accordance with the invention is not limited to specific 2-benzothiazolyl thioesters or to specific acid addition salts of amines. It is of much more general application.

The process in accordance with the invention is especially of great advantage when the amine is not particularly stable in the form of the free base, which is frequently the case especially with 7-amino-cephalosporin derivatives. 7-Acylamino-cephalosporin derivatives can be manufactured in good yield and in high purity with the process in accordance with the invention.

Objects of the present invention are accordingly a process for the acylation of amines with 2-benzothiazolyl thioesters of carboxylic acids, which process comprises reacting the amine in the form of an acid addition salt, as well as the use of this process for the manufacture of carboxylic acid amides, especially of antimicrobially-active 7-acylamino-cephalosporin derivatives.

As already mentioned, the process in accordance with the invention is not limited to specific amines. For example, 6-amino-pencillin derivatives or even simple aliphatic, alicyclic or aromatic amines such as aniline can also be acylated successfully.

The process in accordance with the invention can be carried out in any inert organic solvent in which the starting materials are at least partially soluble. As solvents there come into consideration, for example, the solvents listed hereinafter: halogenated lower hydrocarbons such as methylene chloride, chloroform and carbon tetrachloride, lower N,N-dialkyl fatty acid amides such as N,N-dimethylacetamide and N,N-dimethylformamide, lower alcohols such as methanol and ethanol, lower dialkyl ethers such as diethyl ether, dimethyl ether and t-butyl methyl ether, lower cyclic ethers such as tetrahydrofuran and dioxan, lower mono- and dialkyl ethers of alkanediols such ethylene glycol diethyl ether and ethylene glycol monomethyl ether, lower dialkyl ketones such as acetone and methyl ethyl ketone, dimethyl sulphoxide, mixtures of the previously mentioned solvents and the like.

The halogenated lower hydrocarbons, especially the chlorinated lower hydrocarbons, the lower alcohols and the lower N,N-dialkyl fatty acid amides are preferred solvents. Methylene chloride is a particularly preferred solvent.

The process in accordance with the invention can be carried out in a wide temperature range. It can, for example, be carried out in a range of about 0° C. to about 60° C. The reaction is preferably carried out in a temperature range of about 15° C. to about 30° C., whereby in a particularly preferred embodiment it is carried out at room temperature.

As acid addition salts there come into consideration not only salts with inorganic acids, but also salts with organic acids. Acid addition salts with aromatic or aliphatic sulphonic acids or mineral acids are preferably used. In an especially preferred embodiment acid addition salts with p-toluenesulphonic acid or hydrochloric acid are used.

As the amine there is preferably used a compound of the formula

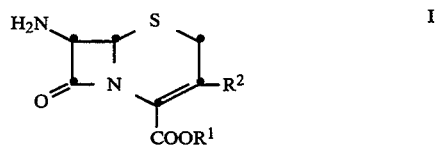

wherein $R^1$ is hydrogen or a group which is usual for blocking the 4-carboxy group of cephalosporins such as those mentioned hereinbelow and $R^2$ is hydrogen or a group which is usual for the 3-position of cephalosporins such as those mentioned hereinbelow.

The amines of formula I are known compounds or can be prepared in accordance with known methods.

In an especially preferred embodiment there are used amines of formula I above in which $R^1$ is hydrogen or the group —A—OCOR. A is lower alkylidene, R is lower alkyl or lower alkoxy, $R^2$ is hydrogen, halogen, lower alkyl, lower alkenyl, lower alkanoyloxyalkyl, lower azidoalkyl, lower carbamoyloxyalkyl or the group —CH$_2$S—Q, —CH=CH—S—Q or —CH$_2$—Q', Q is a heterocyclic group bonded via a carbon atom and Q' is a N-containing heterocyclic group bonded via a nitrogen atom, whereby the heterocyclic groups are groups which are usual in cephalosporins.

As the 2-benzothiazolyl thioester of carboxylic acids there is preferably used a compound of the formula

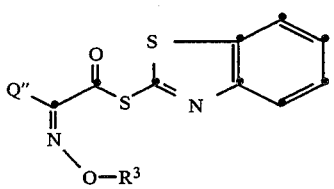

II wherein R³ is lower alkyl, lower alkenyl, lower alkanoyl or the group —A′—COOR′. A′ is lower alkylene, R′ is a carboxy protecting group which is usual in cephalosporin chemistry such as a tertiary lower alkyl, a p-nitrobenzyl, a diphenylmethyl or a tri (lower alkyl)silyl group and Q″ is a heteroaromatic group bonded via a carbon atom, whereby the heteroaromatic group is a group which is usual in 7-oxyiminoacetylamino-cephalosporins. The compounds of formula II are known compounds or can be prepared in accordance with known methods.

In an especially preferred embodiment there is used a compound of formula II above in which R³ is methyl or the group —A′—COOR′, A′ is methylene or 2,2-propylene. R′ is t-butyl and Q″ is 2-amino-4-thiazolyl or 2-furanyl.

In the reaction of an acid addition salt of an amine of formula I with a compound of formula II there is firstly obtained a compound of the formula

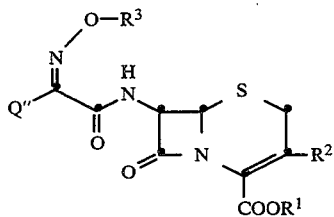

III wherein R¹, R², R³ and Q″ are as described above or, where an amino group which is capable of salt formation is present, the corresponding acid addition salt. These compounds are known compounds which have antimicrobial properties or which can be converted according to known methods into antimicrobially-active compounds.

The antimicrobially-active 7-acylamino-cephalosporin derivatives, which can be made in accordance with the invention in a preferred embodiment, are the compounds of the formula

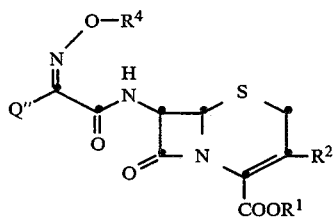

IV wherein R⁴ is hydrogen, lower alkyl, lower alkenyl or the group —A′—COOH and R¹, R², A′ and Q″ as described above and the pharmaceutically acceptable salts thereof.

In a particularly preferred embodiment methylene (6R,7R)-7-amino-3-[(5-methyl-2H-tetrazol-2-yl)methyl]-8-oxo-5-thia-1-azabicyclo[4.2.0]oct-2-ene-2-carboxylate pivalate is used as the amine and (Z)-2-(2-amino-4-thiazolyl)-2-(methoxyimino)acetic acid 2-benzthiazolyl thioester is used as the 2-benzthiazolyl thioester, there being obtained an acid addition salt of methylene (6R,7R)-7-[(Z)-2-(2-amino-4-thiazolyl)-2-(methoxyimino)acetamido]-3-[(5-methyl-2H-tetrazol-2-yl)methyl]-8-oxo -5-thia-1-azabicyclo[4.2.0]oct-2-ene-2-carboxylate pivalate.

As used herein, the term "lower" denotes residues and compounds with up to 7, preferably up to 4, carbon atoms. The term "alkyl", taken alone or in combinations such as alkoxy, alkylene, alkylidene and azidoalkyl, denotes straight-chain or branched, saturated hydrocarbon residues such as methyl, ethyl, isopropyl and s-butyl. The term "alkenyl" denotes straight-chain and branched, unsaturated hydrocarbon residues such as allyl. The term "alkanoyl" denotes straight-chain or branched fatty acid residues such as acetyl.

The term "heteroaromatic" preferably denotes monocyclic heteroaromatic groups which preferably contain an oxygen or sulphur atom and/or 1–4 nitrogen atoms as the hetero atom(s). They are preferably 5- or 6-membered. They can be optionally substituted, whereby amino and lower alkyl groups, for example, come into consideration as substituents. 2-Furanyl, 2-amino-4-thiazolyl and 5-methyl-1,3,4-thiadiazol-2-yl are examples of heretoaromatic groups.

The term "heterocyclic group" preferably denotes monocyclic, especially 5- and 6-membered, partially unsaturated or aromatic heterocyclic groups which preferably contain an oxygen or sulphur atom and/or 1–4 nitrogen atoms as the hereto atom(s) or bicyclic, especially 8- to 10-membered, partially unsaturated or aromatic heterocyclic groups which preferably contain an oxygen or sulphur atom and/or 1–5 nitrogen atoms as the hereto atom(s). These groups are preferably unsubstituted or substituted by hydroxy, oxo, lower alkyl and/or lower oxoalkyl. Thiazolyl, thiadiazolyl, triazinyl, pyridyl, triazolo[1,5-a]pyrimidyl and tetrazolyl are examples of heterocyclic groups.

The term "N-containing heterocyclic group" preferably denotes saturated, partially unsaturated and aromatic heterocyclic groups which contain up to 4 nitrogen atoms as the hereto atom(s). They are preferably 5- or 6-membered and can be annelated by a 5- or 6-membered cycloalkane or benzene ring. They are preferably unsubstituted or substituted by lower alkyl or carbamoyl. The nitrogen atom via which the N-containing heterocyclic group is bonded can also be quaternary substituted. 5-Methyl-2-tetrazolyl and pyridinium-1-yl are examples of N-containing heterocyclic groups.

Useful carboxylic acid amides can be made in accordance with the process of the invention, and, in particular, 7-acylamino-cephalosporin derivatives, which are useful as anti-microbial agents, can be made in accordance with the process of the invention.

The following Examples illustrate the present invention in more detail, but do not limit it.

EXAMPLE 1 a) 8.77 g of (6R,7R)-7-amino-3-methyl-8-oxo-5-thia-1-azabicyclo[4.2.0]oct-2-ene-2-carboxylic acid are suspended in 60 ml of acetone, treated within 15 minutes at 20°–25° C. while stirring with 6.3 g of 1,8-diazabicyclo-[5.4.0]undec-7-ene (DBU), 10.6 g of pivalogyloxymethyl iodide are added to the resulting solution at 15° C. and the mixture is stirred for 15 minutes without cooling. 250 ml of n-butyl acetate are then added thereto, whereupon crystallized-out DBU hydroiodide is filtered off under suction and rinsed with 50 ml of n-butyl acetate. The yellow filtrate is washed twice with 125 ml of saturated sodium chloride solution and filtered through a fluted filter.

100 ml of solvent are distilled off on a water-jet vacuum at 35° C. The solution is again filtered and treated while stirring with 8.4 g of p-toluenesulphonic acid.-H$_2$O, whereby the product crystallizes out. After stirring for 30 minutes the product is filtered off under suction, washed with n-butyl acetate and n-hexane and dried overnight in a water-jet vacuum at 35° C. There are obtained 18.5 g (92.36%) of methylene (6R,7R)-7-amino-3-methyl-8-oxo-5-thia-1-azabicyclo[4.2.0]oct-2-ene-2-carboxylate pivalate p-toluenesulphonate as white crystals (C$_{14}$H$_{20}$N$_2$O$_5$S.C$_7$H$_8$SO$_3$; MW: 500.581).

|   | Microanalysis: | |
|---|---|---|
|   | Calc. | Found |
| C | 50.39 | 50.45 |
| H | 5.64 | 5.78 |
| N | 5.60 | 5.44 | b) 10.02 g of methylene (6R,7R)-7-amino-3-methyl-8-oxo-5-thia-1-azabicyclo[4.2.0]oct-2 -ene-2-carboxylate pivalate p-toluenesulphonate are dissolved in 100 ml of methylene chloride, whereupon the solution is treated with 7.0 g of S-(2-benzothiazolyl)-2-amino-4-thiazole-thio-glyoxylate (Z)-O-methyl oxime, stirred at 20°–25° C. for about 1.5 hours. The resulting solution is washed twice with 50 ml of 5 per cent sodium acetate solution each time and once with 50 ml of water, filtered through a fluted filter and evaporated in a water-jet vacuum at 30° . The residue is dissolved in 100 ml of isopropanol with the addition of 4.5 ml of 5.2N hydrochloric acid in isopropanol. The mixture is stirred at 20°–25° C. for 15 minutes, whereby massive crystallization occurs. 100 ml of n-hexane are added dropwise thereto within 30 minutes while stirring, crystallized-out material is filtered off, washed with isopropanol/n-hexane (1:1) and n-hexane and dried overnight in a water-jet vacuum at 40° C. There are obtained 10.25 g (93.5%) of methylene (6R,7R)-7-[(Z)-2-(2-amino-4-thiazolyl)-2-(methoxyimino)acetamido]-3-methyl-8oxo-5thia-1-azabicyclo[4.2.0]oct-2-ene-2-carboxylate pivalate hydrochloride as colourless crystals. This material is dissolved in 50 ml of ethanol at 40° C. 30 ml of n-hexane are then added dropwise thereto and the mixture is left to crystallize for 15 minutes while stirring. After the dropwise addition of a further 20 ml of n-hexane the product is filtered off under suction, washed with ethanol/n-hexane (1:1) and n-hexane and dried in a water-jet vacuum at 40° C. There are obtained 8.9 g (86.8%) of the desired product. (C$_{20}$H$_{25}$N$_5$O$_7$S$_2$.HCl;

|   | Microanalysis: | |
|---|---|---|
|   | Calc. | Found |
| C | 43.83 | 43.85 |
| H | 4.78 | 4.86 |
| N | 12.78 | 12.83 |

EXAMPLE 2 a) 22.3 g of (6R7R)-7-amino-3-acetoxymethyl-8-oxo-5-thia-1-azabicyclo[4.2.0oct-2-ene-2-carboxylic acid are suspended in 120 ml of acetone, whereupon the suspension is treated within 15 minutes while stirring at 20°–25° C. with 12.6 g of 1,8-diazabicyclo[5.4.0]undec-7-ene (DBU). 21.2 g of pivaloyloxymethyl iodide are added to the resulting solution at 15° C. and the mixture is stirred for a further 15 minutes without cooling. 500 ml of n-butyl acetate are now added, whereupon crystallized-out DBU hydroiodide is filtered off under suction and washed with 100 ml of n-butyl acetate. The yellow filtrate is washed twice with 250 ml of saturated sodium chloride solution each time and filtered through a fluted filter. 200 ml of solvent are distilled off in a water-jet vacuum at 35° C. The solution obtained is again filtered and treated while stirring with 16.8 g of p-toluenesulphonic acid . H$_2$O, whereby the product crystallizes out. After stirring for 30 minutes the product is filtered off under suction, washed with n-butyl acetate and n-hexane and dried overnight in a water-jet vacuum at 35° C. There are obtained 38.7 g (86.6%) of methylene (6R,7R)-3-(acetoxymethyl)-7-amino-8-oxo-5-thia-1-azabicyclo[4.2.0]oct-2-ene-2-carboxylate pivalate p-toluenesulphonate as colourless crystals (C$_{16}$H$_{22}$N$_2$O$_7$S. C$_7$H$_8$SO$_3$; MW: 558.617).

|   | Microanalysis: | |
|---|---|---|
|   | Calc. | Found |
| C | 49.45 | 49.52 |
| H | 5.41 | 5.55 |
| N | 5.01 | 4.95 | b) 5.58 g of methylene (6R,7R)-3-(acetoxymethyl)-7-amino-8-oxo-5-thia-1-azabicyclo[4.2.0]oct-2-ene-2-carboxylate pivalate p-toluenesulphonate are stirred in 60 ml of methylene chloride for 2 hours at 20°–25° C. together with 3.5 g of S-(2-benzothiazolyl)-2-amino-4-thiazole-thio-glyoxylate (Z)-O-methyl oxime. The resulting solution is washed twice with 30 ml of 5 percent sodium acetate solution and once with 30 ml of water, filtered through a fluted filter and evaporated in a water-jet vacuum at 40° C. The residue is dissolved in 50 ml of ethyl acetate with the addition of 2.5 ml of 5.2N hydrochloric acid in isopropanol. 100 ml of ether are added thereto, whereby a resinous material separates. The supernatant liquid is decanted off, and the resin is dissolved in 50 ml of ethyl acetate and crystallized by the slow addition of ether. The product is filtered off under suction, washed with ether and petroleum ether and dried overnight in a water-jet vacuum at 30° C. There are obtained 3.7 g (61%) of methylene 3-(acetoxymethyl)-(6R,7R)-7-[(Z)-2-(2-amino-4-thiazolyl)-2-(methoxyimino)acetamido]-8-oxo-5-thia-1azabicyclo[4.2.0-.]oct-2-ene-2-carboxylate hydrochloride as beige crystals (C$_{22}$H$_{27}$N$_5$O$_9$S$_2$.HCl; MW: 606.065).

|   | Microanalysis: | |
|---|---|---|
|   | Calc. | Found (H$_2$O-free) |
| C | 43.60 | 43.81 |
| H | 4.66 | 4.72 |
| N | 11.56 | 11.58 |

EXAMPLE 3 a) 11.5 g of (6R,7R)-7-amino-3-azidomethyl-8-oxo-5-thia-1-azabicyclo[4.2.0]oct-2-ene-2-carboxylic acid are suspended in 250 ml of methylene chloride. The suspension is treated at 20°–25° C. while stirring with 6.5 g of 1,8-diazabicyclo[5.4.0]undec-7-ene (DBU). After stirring for 15 minutes 10.9 g of pivaloyloxymethyl iodide are added to the dark suspension and the mixture is stirred at 20°–25° C. for 20 minutes. 200 ml of water are now added thereto and the emulsion is filtered through a filter aid. The organic phase is separated, washed twice with 100 ml of water each time and treated with 250 ml of n-butyl acetate, whereupon 250 ml of solvent are distilled off in a water-jet vacuum at 25° C. The solution is filtered through a fluted filter and the filtrate is treated while stirring with 7.6 g of p-toluenesulphonic acid.$H_2O$. After stirring for 30 minutes crystallized-out material is filtered off under suction, washed with n-butyl acetate and low-boiling petroleum ether and dried overnight in a water-jet vacuum at 35° C. There are obtained 11.5 g (53.10%) of methylene (6R,7R)-7-amino-3-(azidomethyl)-8-oxo-5-thia-1-azabicyclo[4.2.0]oct-2-ene-2-carboxylate pivalate p-toluenesulphonate as beige crystals ($C_{14}H_{19}N_5O_5S.C_7H_8SO_3$; MW: 541.594).

|   | Microanalysis: | |
|---|---|---|
|   | Calc. | Found |
| C | 46.57 | 47.02 |
| H | 5.03 | 5.18 |
| N | 12.93 | 12.49 | b) 5.42 g of methylene (6R, 7R)-7-amino-3-(azidomethyl)-8-oxo-5-thia-1-azabicyclo[4.2.0]oct-2-ene-2-carboxylate pivalate p-toluenesulphonate are suspended in 50 ml of methylene chloride, whereupon the suspension is treated with 3.5 g of S-(2-benzothiazolyl)-2-amino-4-thiazolethioglyoxylate (Z)-O-methyl oxime and stirred at 20°–25° C. for 2 hours. The resulting solution is washed twice with 50 ml of 5 percent sodium acetate solution each time and once with 50 ml of water, filtered through a fluted filter and evaporated in a water-jet vacuum at 30°. The residue is dissolved in 50 ml of ethyl acetate with the addition of 2.5 ml of 5.2N hydrochloric acid in isopropanol. 150 ml of ether are added while stirring, whereupon amorphous separated material is filtered off under suction. A solution of the material obtained in 50 ml of ethyl acetate is poured into 150 ml of ether while stirring. The amorphous separated material is filtered off under suction, washed with ether and low-boiling petroleum ether and dried overnight in a high vacuum at 30°. There are obtained 5.0 g (84.75%) of methylene (6R,7R)-7-[(Z)-2-(2-amino-4-thiazolyl)-2-(methoxyimino)acetamido]-3-(azidomethyl)-8-oxo-5-thia-1-azabicyclo[4.2.0]oct-2-ene-2-carboxylate pivalate hydrochloride as a beige amorphous solid ($C_{20}H_{24}N_8O_7S_2.HCl$; MW: 589.042).

|   | Microanalysis: | |
|---|---|---|
|   | Calc. | Found |
| C | 40.78 | 40.84 |
| H | 4.28 | 4.35 |
| N | 19.02 | 18.74 |

EXAMPLE 4 a) 15.6 g of 7-amino-3-[[(5-methyl-1,3,4-thiadiazol-2-yl)thio]methyl]-8-oxo-5-thia-1-azabicyclo[4.2.0oct-2-ene-2-carboxylic acid are suspended in 250 ml of methylene chloride, whereupon the suspension is treated while stirring at 20°–25° with 6.5 g of 1,8-diazabicyclo-[5.4.0]undec-7-ene (DBU). After stirring for 15 minutes 10.9 g of pivaloyloxymethyl iodide are added thereto. The mixture is stirred at 20°–25° for 20 minutes, 250 ml of water are added thereto and the emulsion is filtered through a filter aid. The organic phase is separated, washed with 250 ml of water and treated with 500 ml of n-butyl acetate, whereupon the mixture is concentrated to a volume of 400 ml in a water-jet vacuum at 35°, filtered and the filtrate is treated with 7.6 g of p-toluenesulphonic acid . $H_2O$ while stirring. After stirring for 30 minutes the crystallized-out material is filtered off under suction, washed with n-butyl acetate and low-boiling petroleum ether and dried overnight in a water-jet vacuum at 35°. The material obtained (12.0 g of beige crystals) is dissolved in 100 ml of methylene chloride. The solution obtained is treated with 250 ml of ethyl acetate and concentrated to a volume of 150 ml in a water-jet vacuum at 30°. The crystallized-out material is filtered off under suction, washed with ethyl acetate and low-boiling petroleum ether and dried overnight in a water-jet vacuum at 30°. There are obtained 8.2 g (32.5%) of methylene (6R,7R)-7-amino-3-[[(5-methyl-1,3,4-thiadiazol-2-yl)thio]methyl]-8-oxo-5-thia-1-azabicyclo-[4.2.0]oct-2-ene-2-carboxylate p-toluenesulphonate as white crystals ($C_{17}H_{22}N_4O_5S_3.C_7H_8SO_3$: MW: 630.764).

|   | Microanalysis: | |
|---|---|---|
|   | Calc. | Found |
| C | 45.70 | 45.79 |
| H | 4.79 | 4.83 |
| N | 8.88 | 8.74 | b) 6.3 g of methylene (6R,7R)-7-amino-3-[[(5-methyl-1,3,4-thiadiazol-2-yl)thio]methyl]-8-oxo-5-thia-1-azabicyclo [4.2.0]oct-2-ene-2-carboxylate pivalate p-toluenesulphonate are dissolved in 60 ml of methylene chloride. The solution is treated with 3.5 g of S-(2-benzothiazolyl)-2-amino-4-thiazole-thioglyoxylate (Z)-O-methyl oxime, stirred at 20°–25° for 2 hours, the solution is washed twice with 50 ml of 5 percent sodium acetate solution each time and once with 50 ml of water, filtered through a fluted filter and evaporated in a water-jet vacuum at 30°. The residue is dissolved in 100 ml of ethyl acetate. 2.5 ml of 5.2N hydrochloric acid in isopropanol are added thereto while stirring, the separated hydrochloride is filtered off under suction, washed with ethyl acetate and low-boiling petroleum ether and dried overnight in a water-jet vacuum at 30°. The material obtained (6.2 g) is dissolved in 30 ml of acetone. The solution is poured into 150 ml of ether while stirring, the amorphous separated material is filtered off under suction, washed with ether and petroleum ether and dried overnight in a high vacuum at 40°. There are obtained 5.0 g (73.7%) of methylene (6R,7R)-7-[(Z)-2-(2-amino-4-thiazolyl)-2-(methoxyimino)acetamido]-3-[[(5-methyl-1,3,4-thiadiazol-2-yl)thio]methyl]-8-oxo-5-thia 1-azabicyclo[4.2.0]oct-2-ene-2-carboxylate pivalate hydrochloride as a beige amorphous solid ($C_{23}H_{27}N_7O_7S_4$ .HCl: MW: 678.212).

|   | Microanalysis: | |
|---|---|---|
|   | Calc. | Found |
| C | 40.73 | 40.48 |
| H | 4.16 | 4.15 |

| Microanalysis: | | |
|---|---|---|
| | Calc. | Found |
| N | 14.46 | 14.10 |

EXAMPLE 5 a) 12.15 g of (6R,7R)-7-amino-3-(5-methyl-2H-tetrazol-2-yl)-8-oxo-5-thia-1-azabicyclo[4.2.0]oct-2-ene-2-carboxylic acid are suspended in 60 ml of acetone. The suspension is treated within 15 minutes at 20°–25° while stirring with 6.3 g of 1.8-diazabicyclo[5.4.0]undec-7-ene (DBU), 10.6 g of pivaloyloxymethyl iodide are added to the resulting solution at 15° and the mixture is stirred for 15 minutes without cooling. 250 ml of n-butyl acetate are now added thereto. Crystallized-out DBU hydroiodide is filtered off under suction and washed with 50 ml of n-butyl acetate. The yellow filtrate is washed twice with 125 ml of saturated sodium chloride solution each time and filtered through a fluted filter. 100 ml of solvent are distilled off in a water-jet vacuum at 35°. The solution is again filtered and treated while stirring with 8.4 g of p-toluenesulphonic acid . $H_2O$. The crystallized-out material is filtered off under suction after stirring for 30 minutes and washed with n-butyl acetate. The material obtained is suspended in 200 ml of n-butyl acetate and treated while stirring with 20 ml of 5.2N hydrochloric acid in isopropanol, whereby a solution results. This solution is stirred for 1 hour, whereby crystallization occurs. The crystallized-out hydrochloride is filtered off under suction, washed with n-butyl acetate and n-hexane and dried overnight in a water-jet vacuum at 35°. There are obtained 13.9 g (77.75%) of methylene (6R,7R)-7-amino-3-[5-methyl-2H-tetrazol-2-yl)methyl]-8-oxo-5-thia-1azabicyclo[4.2.-0]oct-2-ene-2-carboxylate pivalate hydrochloride as white crystals ($C_{16}H_{22}N_6O_5S$. HCl; MW: 446.91).

| Microanalysis: | | |
|---|---|---|
| | Calc. | Found |
| C | 43.00 | 43.05 |
| H | 5.19 | 5.20 |
| N | 18.81 | 18.62 |
| S | 7.17 | 7.43 |
| Cl | 7.93 | 7.66 | b) 4.46 g of methylene (6R,7R)-7-amino-3-[(5-methyl-2H-tetrazol-2-yl) methyl]-8 -oxo-5-thia-1-azabicyclo[4.2.0]-oct-2-ene-2-carboxylate pivalate hydrochloride are dissolved in 50 ml of methylene chloride. The solution is treated with 4.79 g of S-(2-benzothiazolyl)-2-amino-α-[(Z)-[1-(t-butoxycarbonyl-1-methylethoxy]imino]-4-thiazole-thioacetate and stirred at 20°–25° for 3 hours. The solution is evaporated in a water-jet vacuum at 30° and the residue is dissolved in 50 ml of ethyl acetate. The solution is treated while stirring with 200 ml of ether, whereby a resin separates. The supernatant liquid phase is decanted off. The resin is dissolved in 50 ml of ethyl acetate, whereupon the solution is poured into 300 ml of ether while stirring. The amorphous separated material is filtered off under suction, washed with ether and low-boiling petroleum ether and dried overnight in a water-jet vacuum at 35°. There are obtained 6.55 g (86.4%) of methylene (6R,7R)-7-[(Z)-2-(2-amino-4-thiazolyl)-2-[[1-(t-butoxycarbonyl)-1-methyl ethoxy]imino]acetamido]-3-[(5-methyl-2H-tetrazol-2-yl)methyl]-8-oxo-5-thia-1azabicyclo[4.2.0]oct-2-ene-2-carboxylate pivalate hydrochloride as a beige amorphous solid ($C_{29}H_{39}N_9O_9S_2$.HCl; MW: 758. 266 ).

| Microanalysis: | | |
|---|---|---|
| | Calc. | Found |
| C | 45.94 | 45.73 |
| H | 5.32 | 5.56 |
| N | 16.63 | 16.37 |

Example 6

4.46 g of methylene (6R,7R)-7-amino-3-[(5-methyl-2H-tetrazol-2-yl )methyl]-8-oxo-5-thia-1-azabicyclo[4.2.0]-oct-2-ene-2-carboxylate pivalate hydrochloride are dissolved in 60 ml of methylene chloride. The solution is treated with 4.5 g of S-(2-benzothiazolyl)-2-amino-4-thiazole-thioglyoxylate (Z)-O-[(t-butoxycarbonyl)methyl]oxime and the mixture is stirred at 20°–25° for 3 hours. The solution is evaporated at 30° in a water-jet vacuum. The residue is dissolved in 50 ml of ethyl acetate. The solution is treated while stirring with 200 ml of ether and amorphous separated material is filtered off under suction and washed with ether. The material obtained is dissolved in 30 ml of ethyl acetate. The solution is poured into 300 ml of ether while stirring. The amorphous separated material is filtered off under suction, washed with ether and low-boiling petroleum ether and dried overnight in a water-jet vacuum at 40°. There are obtained 6.2 g (84.9%) of methylene (6R,7R)-7-[(Z)-2-(2-amino-4-thiazolyl)-2-[[t-butoxycarbonyl)methoxyimino]acetamido]-3 -[5-methyl-2H-tetrazol-2-yl)methyl]-8-oxo-5-thia-1--azabicyclo[4.2.0oct-2-ene-2-carboxylate pivalate hydrochloride as a beige amorphous solid ($C_{27}H_{35}N_9O_9S_2$.HCl; MW: 730.212).

| Microanalysis: | | |
|---|---|---|
| | Calc. | Found |
| C | 44.41 | 44.32 |
| H | 4.97 | 5.18 |
| N | 17.26 | 17.00 |

EXAMPLE 7

26.1 g of methylene (6R,7R)-7-amino-3-[(5-methyl-2H-tetrazol-2-yl)methyl]-8-oxo-5-thia-1-azabicyclo[4.2.0]-oct-2-ene-2-carboxylate pivalate hydrochloride are dissolved in 260 ml of methylene chloride. The solution is treated with 20.44 g of S-(2-benzothiazolyl)-2-amino-4-thiazole-thioglyoxylate (Z)-O-methyl oxime, the solution is stirred at 20°–25° for 2 hours and subsequently evaporated in a water-jet vacuum at 30°. The residue is dissolved in 350 ml of acetone. The solution is left to crystallize for 1.5 hours while stirring, the product is filtered off under suction, washed with acetone and n-hexane and dried overnight in a water-jet vacuum at 35°. The material obtained (33.15 g of colourless crystals) is dissolved in 100 ml of methanol, whereupon the solution is treated with 100 ml of ethanol and subsequently with 130 ml of n-hexane, left to crystallize at 20°–25° for 30 minutes, a further 70 ml of n-hexane are added dropwise thereto while stirring within about 30 minutes, the mixture is suction filtered and the material obtained is washed with ethanol/n-hexane (1:1) and dried overnight in a water-jet vacuum at 35°. There are obtained 29.5 g (80.16%) of methylene (6R,7R)-7-[(Z)-2-(2-amino-4thiazoyl)-2-(methoxyimino)acetamido]-3-[(5-methyl-2H-tetrazol-2-yl)methyl]-8-oxo-5-thia-1-azabicyclo[4.2.0]-ozo-2-ene-2-carboxylate pivalate hydrochloride as white crystals ($C_{22}H_{27}N_9O_7S_2$ .HCl; MW: 630.095).

|   | Microanalyis: | |
|---|---|---|
|   | Calc. | Found |
| C | 41.94 | 42.02 |
| H | 4.48 | 4.40 |
| N | 20.01 | 20.14 |

EXAMPLE 8

3.25 g of methylene (2S,5R,6R)-6-amino-3,3-dimethyl-7 -oxo-4-thia-1-azabicyclo[3.2.0]heptane-2-carboxylate pivalate hydrochloride are dissolved in 30 ml of methylene chloride, whereupon the solution is treated with 3.1 g of S-(2-benzothiazolyl)-2-amino-4-thiazole-thioglyoxylate (Z)-O-methyl oxime, stirred at 20°-25° for 2 hours and the solution obtained is filtered through a fluted filter. The filtrate is poured into 200 ml of isopropyl ether while stirring. The amorphous separated material is filtered off under suction, washed with isopropyl ether and dissolved in 250 ml of n-butyl acetate. The solution is then concentrated to a volume of 100 ml in a water-jet vacuum at 30°. 100 ml of ether are added while stirring, the separated material is filtered off under suction, washed with ether and low-boiling petroleum ether and dried overnight in a high vacuum at 40°. There are obtained 3.7 g (76%) of methylene (2S,5R,6R)-6-[(Z)-2-(2-amino-4-thiazolyl)-2-(methoxyimino)acetamido]-3,3-dimethyl-7-oxo-5-thia-1-azabicyclo[3.2.0]heptane-2-carboxylate pivalate hydrochloride as a yellowish amorphous solid.

|   | Microanalysis: | |
|---|---|---|
|   | Calc. | Found (H₂O-free) |
| C | 43.67 | 43.39 |
| H | 5.13 | 5.13 |
| N | 12.79 | 12.91 |

EXAMPLE 9

1.3 g of aniline hydrochoride are suspended in 50 ml of methylene chloride. The suspension is treated with 3.5 g of S-(2-benzothiazolyl)-2-amino-4-thiazole-thioglyoxylate (Z)-O-methyl oxime and stirred at 20°-25° for 1.5 hours, whereby there is obtained a solution from which the desired product crystallizes out. The product is filtered off under suction, washed with methylene chloride and dried in a water-jet vacuum at 30°. The material obtained (3.1 g of beige crystals) is dissolved in 31 ml of methanol in the warm. The solution is cooled to 20° treated with 30 ml of ether, the crystallized-out material is filtered off under suction, washed with methanol/ether (1:1) and ether and dried overnight in a high vacuum at 40°. There are obtained 2.35 g (75.1%) of 2-amino-4thiazoleglyoxylanilide (Z)-O-methyl oxime hydrochloride as beige crystals ($C_{12}H_{12}N_4O_2S$ .HCl; MW: 312.775).

|   | Microanalysis: | |
|---|---|---|
|   | Calc. | Found |
| C | 46.08 | 46.20 |
| H | 4.19 | 4.20 |
| N | 17.91 | 17.98 |

EXAMPLE 10

3.64 g of 1-[[(6R,7R)-7-amino-2-carboxy-8-oxo-5-thia-1-azabicyclo[4.2.0]oct-2-ene-3-yl]methyl-pyridinium hydroxide internal salt dihydrochloride are dissolved in 250 ml of methanol. 5.74 g of S-(2-benzothiazolyl)-2-amino-α-[(Z)-[1-(t-butoxycarbonyl)-1-methylethoxy]-imino]-4-thiazole-thioacetate and 150 ml of methylene chloride are now added thereto and the mixture is stirred at 20°-25° for 2 hours. The yellow solution obtained is evaporated in a water-jet vacuum at 30° and the residue is triturated with 100 ml of acetone. The solid is filtered off under suction, washed with acetone and dried in a vacuum at 25°. The material obtained (5.6 g of a beige amorphous solid) is partitioned between 50 ml of water and 50 ml of methylene chloride. The aqueous phase is separated, washed twice with methylene chloride and lyophilized overnight in a high vacuum. There are obtained 4.2 g (62.2%) of 1-[[( 6R,7R)-7-[(Z)-(2-amino-4-thiazolyl)-2-[[1-(t-butoxycarbonyl)-1-methylethoxy]imino]-acetamido]-2-carboxy-8-oxo-5-thia-1-azabicyclo[4.2.0]oct-2-en-3-yl]methyl]-pyridinium hydroxide internal salt dihydrochloride as a beige lyophilizate ($C_{26}H_{30}N_6O_7S_2.2HCl$; MW: 675.603).

|   | Microanalysis: | |
|---|---|---|
|   | Calc. | Found (H₂O-free) |
| C | 46.22 | 46.29 |
| H | 4.77 | 4.68 |
| N | 12.44 | 12.51 |
| S | 9.49 | 9.43 |
| Cl | 10.50 | 10.48 |

EXAMPLE 11

3.09 g of (6R,7R)-7-amino-3-acetoxymethyl-8-oxo-5 -thia-1-azabicyclo[4.2.0oct-2-ene-2-carboxylic acid hydrochloride are dissolved in 50 ml of N,N'-dimethylacetamide. The solution is treated with 4.2 g of S-(2-benzothiazolyl)-2-amino-4-thiazole-thioglyoxylate (Z)-O-methyl oxime, stirred at 20°-25° for 30 minutes and subsequently evaporated in a high vacuum at 35°. The residue is dissolved in 25 ml of acetone. The solution is poured into 200 ml of ether while stirring, the separated material is filtered off, washed with ether and dried in a water-let vacuum at 30°. The material obtained (6.5 g of yellowish-amorphous solid) is stirred for 1 hour at 25° in 100 ml of isopropanol with the addition of 2 ml of 5N hydrochloric acid in isopropanol, whereby crystallization occurs. The crystals are filtered off under suction, washed with isopropanol and low-boiling petroleum ether and dried overnight in a high vacuum at 30°. There are obtained 3.55 g (72.15%) of (6R,7R)-3-(acetoxymethyl)-7-[2-(2-amino-4-thiazolyl)-2-(methoxyimino)acetamido]-8-oxo-5-thia-1-azabicyclo[4.2.0]oct-2-ene-2-carboxylic acid hydrochloride as beige crystals ($C_{16}H_{17}N_5O_7S_2.HCl.0.3$ isopropanol; MW: 509.95).

| Microanalysis: | | |
|---|---|---|
| | Calc. | Found |
| C | 39.81 | 40.18 |
| H | 4.03 | 4.20 |
| N | 13.73 | 13.77 |

EXAMPLE 12

3.75 g of (6R,7R)-7-amino-3-methyl-8-oxo-5-thia-1-azabicyclo[4.2.0oct-2-ene-2-carboxylic acid hydrochloride are dissolved in-75 ml of N,N'-dimethylacetamide, whereupon the solution is treated with 6.3 g of S-(2-benzothiazolyl)-2-amino-4-thiazole-thioglyoxylate (Z)-O-methyl oxime, stirred at 20°–25° for 30 minutes and subsequently evaporated in a high vacuum at 35°. The residue is triturated with 500 ml of methylene chloride. The separated material is filtered off under suction, washed with methylene chloride and ether and dried in a water-jet vacuum at 25°. The material obtained (6.3 g of almost colourless amorphous solid) is stirred at 20° for 2 hours in 100 ml of isopropanol with the addition of 3 ml of 5N hydrochloric acid in isopropanol, whereby crystallization occurs. The crystals are filtered off under suction, washed with isopropanol and ether and suspended in 40 ml of ethanol. The suspension is stirred at 50° for 30 minutes. It is then cooled to 20° and the solid is filtered off under suction, washed with ethanol and n-hexane and dried overnight in a high vacuum at 30°. There are obtained 2.4 g (37%) of (6R,7R)-7-[(Z)-2-(2-amino-4-thiazolyl)-2-(methoxyimino)acetamido]-3-methyl-8-oxo-5-thia-1-azabicyclo[4.2.0]oct-2-ene-2-carboxylic acid hydrochloride as colourless crystals ($C_{14}H_{15}N_5O_5S_2 \cdot HCl$: MW: 433.885).

| Microanalysis: | | |
|---|---|---|
| | Calc. | Found (H$_2$O-free) |
| C | 38.76 | 39.16 |
| H | 3.72 | 3.71 |
| N | 16.14 | 16.22 |

EXAMPLE 13

2.23 g of methylene (6R,7R)-7-amino-3-[(5-methyl-2H-tetrazol-2-yl)methyl]-8-oxo-5-thia-1-azabicyclo[4.2.0]-oct-2-ene-2-carboxylate pivalate hydrochloride are dissolved in 50 ml of methylene chloride, whereupon the solution is treated with 2.71 g of (S)-(2-benzothiazolyl)-thiobenzoate, stirred at 20°–25° for 24 hours and the solution is evaporated in a water-jet vacuum at 30°. The residue is triturated with 25 ml of ether for 1 hour. The product is filtered off under suction and washed with ether. The material is dissolved in 40 ml of methylene chloride, 80 ml of isopropyl ether are added thereto and the solvent is distilled off in a water-let vacuum at 30°. The crystals are filtered off under suction, washed with isopropyl ether and dried overnight in a high vacuum at 30°. There are obtained 1.2 g (46.7%) of methylene (6R,7R)-7-benzamido-3-[(5-methyl-2H-tetrazol-2-yl)-methyl]-8-oxo-5-thia-1-azabicyclo[4.2.0]oct-2-ene-2-carboxylate pivalate as white crystals ($C_{23}H_{26}N_6O_6S$; MW: 514.557).

| Microanalysis: | | |
|---|---|---|
| | Calc. | Found |
| C | 53.69 | 53.40 |
| H | 5.09 | 5.26 |
| N | 16.33 | 16.24 |

We claim:

1. A process for the preparation of an amide of a penicillin or cephalosporin derivative which comprises reacting a 6-aminopenicillin derivative or a 7-aminocephalosporin derivative of the formula

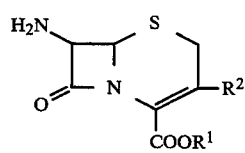

wherein $R^1$ is hydrogen or the group —A—OCOR, A is lower alkylidene, R is lower alkyl or lower alkoxy and $R^2$ is hydrogen, halogen, lower alkyl, lower alkenyl, lower alkanoyloxyalkyl, lower azidoalkyl, lower carbamoyloxy alkyl or the group —CH$_2$—S—Q, —CH=CH—S—Q, Q is a heterocyclic group bonded via a carbon atom wherein the heterocyclic group is a monocyclic 5- or 6-membered, partially unsaturated or heterocyclic group containing 1–4 nitrogen atoms or an oxygen or sulphur atom and 1–4 nitrogen atoms; or a bicyclic 8- to 10-membered, partially unsaturated or aromatic heterocyclic group containing 1–5 nitrogen atoms or an oxygen or sulphur atom and 1–5 nitrogen atoms, in the form of an acid addition salt with its amino moiety with a 2-benzothiazolyl thioester of the formula

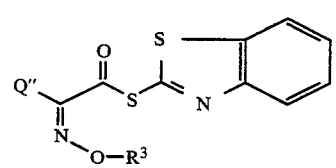

wherein $R^3$ is lower alkyl, lower alkenyl, lower alkanoyl or the group —A'—COOR', A' is lower alkylene, R' is a carboxy protecting group and Q" is a heteroaromatic group bonded via a carbon atom, to obtain the corresponding amide.

2. A process for the preparation of an amide of a penicillin or cephalosporin derivative which comprises reacting a 6-aminopenicillin derivative or a 7-aminocephalosprin derivative of the formula

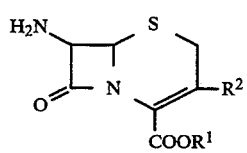

wherein $R^1$ is hydrogen or the group —A—OCOR, A is lower alkylidene, R is lower alkyl or lower alkoxy and $R^2$ is lower alkyl in the form of an acid addition salt with its amino moiety with a 2-benzothiazolyl thioester of the formula

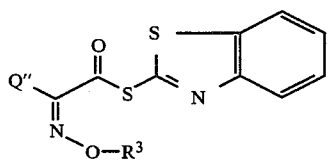

wherein R³ is lower alkyl, lower alkenyl, lower alkanoyl or the group —A'—COOR', A' is lower alkylene, R' is a carboxy protecting group and Q" is a heteroaromatic group bonded via a carbon atom, to obtain the corresponding amide.

3. A process for the preparation of an amide of a cephalosporin derivative which comprises reacting a 7-aminocephalosporin derivative of the formula

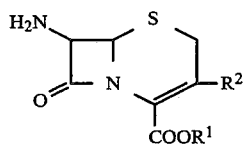

wherein R¹ is hydrogen or the group —A—OCOR, A is lower alkylidene, R is lower alkyl or lower alkoxy and R² is hydrogen, halogen, lower alkyl, lower alkenyl, lower alkanoyloxyalkyl, lower azidoalkyl, lower carbamoyloxy alkyl or the group —CH₂—S—Q, —CH=CH—S—Q, Q is a heterocyclic group bonded via a carbon atom wherein the heterocyclic group is a monocyclic 5- or 6-membered, partially unsaturated or heterocyclic group containing 1-4 nitrogen atoms or an oxygen or sulphur atom and 1-4 nitrogen atoms; or a bicyclic 8- to 10-membered, partially unsaturated or aromatic heterocyclic group containing 1-5 nitrogen atoms or an oxygen or sulphur atom and 1-5 nitrogen atoms, in the form of an acid addition salt with its amino moiety with a 2-benzothiazolyl thioester of the formula

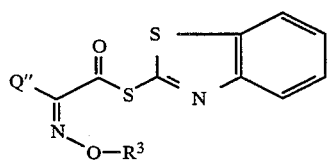

wherein R³ is lower alkyl, lower alkenyl, lower alkanoyl or the group —A'—COOR', A' is lower alkylene, R' is a carboxy protecting group and Q" is a heteroaromatic group bonded via a carbon atom, to obtain the corresponding amide.

4. A process for the preparation of an amide of a cephalosporin derivative which comprises reacting a 7-aminocephalosporin derivative of the formula

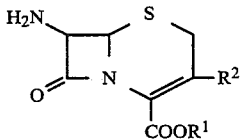

wherein R¹ is hydrogen or the group —A—OCOR, A is lower alkylidene, R is lower alkyl or lower alkoxy and R² is lower alkyl in the form of an acid addition salt with its amino moiety with a 2-benzothiazolyl thioester of the formula

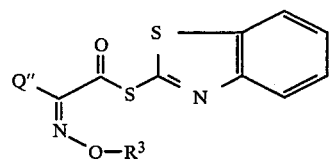

wherein R³ is lower alkyl, lower alkenyl, lower alkanoyl or the group —A'—COOR', A' is lower alkylene, R' is a carboxy protecting group and Q" is a heteroaromatic group bonded via a carbon atom, to obtain the corresponding amide.

5. The process of claim 1, wherein Q" is 2-furanyl, 2-amino-4-thiazolyl or 5-methyl- 1,3,4-thiadiazol-2-yl.

6. A process according to claim 1, wherein R³ is methyl or the group —A'—COOR', A' is methylene or 2,2-propylene, R' is t-butyl and Q" is 2-amino-4-thiazolyl or 2-furanyl.

7. A process according to claim 1, wherein the amine is methylene (6R,7R)-7-amino-3-[(5-methyl-2H-tetrazol-2-yl)methyl]-8-oxo-5-thia-1-azabicyclo[4.2.0]oct-2-ene-2-carboxylate pivalate and the benzothiazolyl thioester is (Z)-2-(2-amino-4-thiazolyl)-2-(methoxyimino) acetic acid 2-benzothiazolyl thioester.

8. A process according to claim 1, wherein an acid addition salt with an aromatic aliphatic or sulphonic acid or a mineral acid is used.

9. A process according to claim 1, wherein an acid addition salt with p-toluenesulphonic acid or hydrochloric acid is used.

10. A process according to claim 1, wherein a lower alcohol, a halogenated lower hydrocarbon or a lower N,N-dialkyl fatty acid amide is used as the solvent.

11. A process according to claim 1, wherein the reaction is carried out in a temperature range of 15°–30° C.

* * * * *